United States Patent [19]

Uchtman

[11] Patent Number: 4,812,311

[45] Date of Patent: * Mar. 14, 1989

[54] KIT FOR USE IN THE TREATMENT OF OSTEOPOROSIS

[75] Inventor: Vernon A. Uchtman, Cincinnati, Ohio

[73] Assignee: The Procter & Gamble Company, Cincinnati, Ohio

[ * ] Notice: The portion of the term of this patent subsequent to Mar. 14, 2006 has been disclaimed.

[21] Appl. No.: 906,859

[22] Filed: Sep. 12, 1986

Related U.S. Application Data

[63] Continuation of Ser. No. 684,560, Dec. 21, 1984, abandoned, which is a continuation-in-part of Ser. No. 605,540, Apr. 30, 1984, abandoned.

[51] Int. Cl.$^4$ .................. A61K 31/66; A61K 35/55
[52] U.S. Cl. ................... 424/112; 424/128; 424/151; 514/141; 514/167
[58] Field of Search .......... 424/128, 112; 514/167, 514/141

[56] References Cited

U.S. PATENT DOCUMENTS

| | | | |
|---|---|---|---|
| 3,683,080 | 8/1972 | Francis | 424/204 |
| 4,230,700 | 10/1980 | Francis | 424/204 |
| 4,330,537 | 5/1982 | Francis | 424/204 |

FOREIGN PATENT DOCUMENTS

| | | |
|---|---|---|
| 110294 | 6/1984 | European Pat. Off. |
| 3243358 | 5/1984 | Fed. Rep. of Germany |

OTHER PUBLICATIONS

Anderson et al., "Preliminary Observations of a Form Coherence Therapy for Osteoporosis", *Calcif. Tissue Int.*, vol. 36 (1984), pp. 341-343.

Frost, "*Editorial*—The ADFR Concept Revisited", *Calcif. Tissue Int.*, vol. 36 (1984), pp. 349-353.

Hodsman et al., "Clinical Studies of Patients Currently Enrolled in Cyclical (ADFR) Therapy for Osteoporosis", abstract from Feb. 1984 meeting in London Ont.

Copy of slide "Coherence Therapy Trial" projected on a screen during Dr. Anderson's talk at the Sun Valley meeting, Aug., 1983.

Recker, "Stimulation of New Bone Formation by the 'ADER' Technique in Dogs,", in *Bone Histomorphometry 1980*, (Jee and Parifitt Editors), Armour-Montagu, Levallois (1981), pp. 331-336.

Chestnut, "Synthetic Salmon Calcitonin, Diphosphonates, and Anabolic Steroids in the Treatment of Postmenopausal Osteoporosis", Osteoporosis-Proceedings of the Copenhagen International Symposium on Osteoporosis, Jun. 3-8, 1984, (Christiansen et al., Editors), Aalborg Stiftsbogtrykkeri (1984), pp. 549-555, see pp. 551-552.

Adami et al., "Dichloromethylene-Diphosphonate Therapy of Osteolytic Lesions and Osteoporosis", Osteoporosis-Proceedings of the Copenhagen International Symposium on Osteoporosis, Jun. 3-8, 1984, (Christiansen et al., Editors), Aalborg Stiftsbogtrykkeri (1984), pp. 643-645.

Reeve et al., "Studies of a 'Short-Cycle' ADFR Regime Using Parathyroid Peptide hPTH 1-34 in Idiopathic Osteoporosis and in a Dog Model," Osteoporosis-Proceedings of the Copenhagen International Symposium on Osteoporosis, Jun. 3-8, 1984 (Christiansen et al., Editors), Aalborg Stiftsbogtrykkeri (1984) pp. 567-573.

Rasmussen et al., "Effect of Combined Therapy with Phosphate Calcitonin on Bone Volume in Osteoporosis," *Metab. Bone Dis. & Rel. Res.*, vol. 2 (1980) pp. 107-111.

Rasmussen, "Considerations as to the Pathogenesis and Treatment of Osteoporosis" in *Bone Histomorphometry 1980*, (Jee and Parifitt Editors), Armour-Montagu, Levallois (1981), pp. 311-316.

Marie et al., "Treatment of Postmenopausal Osteoporosis with Phosphate and Intermittent Calcitonin", Osteoporosis-Proceedings of the Copenhagen International Symposium on Osteoporosis, Jun. 3-8, 1984, (Christiansen et al., Editors), Aalborg Stiftsbogtrykkeri (1984), pp. 575-579.

Berthel et al., "Treatment of Post Menopausal Osteoporosis with Phosphate and Intermittent Calcitonin; Effect on Cortical Bone", Osteoporosis—Proceedings of the Copenhagen International Symposium on Osteoporosis, Jun. 3-8, 1984 (Christiansen et al., Editors), Aalborg Stiftsbogtrykkeri (1984) pp. 651-652.

Ortolani et al., "Treatment of Postmenopausal and Senile Osteoporosis with Combined Calcitonin and 1.25-Dihydroxycholecalciferol", Osteoporosis—Proceedings of the Copenhagen International Symposium on Osteoporosis, Jun. 3-8, 1984, Christiansen et al., Editors), Aalborg Stiftsbogtrykkerri (1984), pp. 625-628.

Geusens and Dequeker, "Effect of Anabolic Steroids, 1-alpha Hydroxyvitamin D and Intermittent Calcium Infusions on Bone Mineral Content in Osteoporosis," Osteoporosis-Proceedings of the Copenhagen International Symposium on Osteoporosis, Jun. 3-8, 1984, (Christiansen et al., Editors) Aalborg Stiftsbogtrykkeri (1984) pp. 665-667.

Delmas et al., "Cyclic Fluoride Therapy for Postmenopausal Osteoporosis", Osteoporosis-Proceedings of the Copenhagen International Symposium on Osteoporosis, Jun. 3-8, 1984, (Christiansen et al., Editors), Aalborg Stiftsbogtrykkeri (1984) pp. 581-586.

(List continued on next page.)

*Primary Examiner*—Leonard Schenkman
*Attorney, Agent, or Firm*—Milton B. Graff, IV; Steven J. Goldstein; Jack D. Schaeffer

[57] ABSTRACT

A kit for use in the treatment of osteoporosis is disclosed. The kit comprises a bone cell activating compound, a bone resorption inhibiting polyphosphonate, and a nutrient supplement or placebo, for sequential administration.

17 Claims, No Drawings

OTHER PUBLICATIONS

Meunier et al., "Treatment of Primary Osteoporosis with Drugs that Increase Bone Formation: Sodium Fluoride, hPTH 1-34, ADFR Concept," Osteoporosis-Proceedings of the Copenhagen International Symposium on Osteoporosis, Jun. 3-8, 1984, (Christiansen et al., Editors), Aalborg Stiftsbogtrykkeri (1984) pp. 595-602.

Kleerekoper et al., "Treatment of Osteoporosis with Sodium Fluoride Alternating with Calcium and Vitamin D", Osteoporosis: Recent Advances in Pathogenesis and Treatment (DeLuca et al., Editors), University Park Press, Baltimore, MD (1981) pp. 441-448.

Briancon and Meunier, "Treatment of Osteoporosis with Fluoride, Calcium, and Vitamin D", *Orthop. Clin. N. Amer.*, vol. 12 (1981), pp. 629-648.

Siris et al., "Long-Term Therapy of Paget's Disease of Bone with EHDP", *Arthritis and Rheumatism*, 23(10), pp. 1177-1184 (1980).

Meunier et al., "Effects of Disodium Dichloromethylene Diphosphonate on Paget's Disease of Bone," *Adv. Exp. Med. Biol.*, 128, pp. 299-309 (1980).

Bonjour et al., "Action of 1,25-Dihydroxyvitamin $D_3$ and a Diphosphonate on Calcium Metabolism in Rats", *Amer. J. Physiology*, vol. 229 (1975), pp. 402-408.

Bonjour et al., "Influence of 1,25-Dihydroxycholecalciferol and Diphosphonate on Calcium Metabolism", *Experientia*, vol. 29(1973), p. 740.

Boris et al., "Evidence for the Promotion of Bone Mineralization by 1-alpha, 25-Dihydroxycholecalciferol in the Rat Unrelated to the Correction of Deficiencies in Serum Calcium and Phosphorus", *J. Nutr.*, vol. 108 (1978), pp. 1899-1906.

Mallon, et al., "Effect of Diphosphonates on Bone Mineralization and Serum Levels of 1-alpha, 25-dihydroxyvitamin D in Rats," *Proceedings of the Workshop on Vitamin D*, 1982, 809-811 (1982).

Mallon, et al., "Effect of Diphosphonates on Bone Mineralization and Serum Levels of 1-alpha, 25-dihydroxyvitamin D in Rats", abstract from the Fifth Workshop on Vitamin D, Historic Williamsburg, Virginia, Feb. 14-19, 1982.

Frost, "Treatment of Osteoporoses by Manipulation of Coherent Bone Cell Population" *Clin. Orth. Rel. Res.*, vol. 143(1979), pp. 227-244.

Frost, "The ADFR Concept and Monitoring It", in *Bone Histomorphometry* 1980, (Jee and Parifitt, Editors), Armour-Montagu, Levallois (1981), pp. 317-321.

Frost, "The Evolution of Osteoporosis Therapy", *Orthop. Clin. N. Amer.* vol. 12 (1981), pp. 603-610.

Frost, "Coherence Treatment of Osteoporoses", *Orthop. Clin. N. Amer.*, vol. 12 (1981), pp. 649-669.

Frost, "Clinical Management of Symptomatic Osteoporotic Patient", *Orthop. Clin. N. Amer.*, vol. 12 (1981), pp. 671-681.

Frost, "Osteoporoses: Quo Vadis?", *Orthop. Clin. N. Amer.*, vol. 12 (1981), pp. 683-691.

Frost, "*Review Article*—The Skeletal Intermediary Organization", *Metab. Bone Dis. & Rel. Res.*, vol. 4 (1983), pp. 281-290.

Francis and Martodam, "Ch. 4-Chemical, Biochemical, and Medicinal Properties of the Diphosphonates," in *The Role of Phosphonates in Living Systems*, (Hildebrand, Editor), CRC Press, Inc., Boca Raton, Fla. (1983), pp. 55-96.

Recker, "Continuous Treatment of Osteoporosis: Current Status", *Orthop. Clin. N. Amer.*, vol. 12 (1981), pp. 611-627.

Hesch, et al.; *Acta Endocr. (Kobenhavn)*, 108 (267, suppl), pp. 171-172 (1985).

KIT FOR USE IN THE TREATMENT OF OSTEOPOROSIS

CROSS REFERENCE TO RELATED APPLICATIONS

This is a continuation of application Ser. No. 684,560, filed Dec. 21, 1984, which is a continuation-in-part of application Ser. No. 605,540 filed Apr. 30, 1984, both abandoned.

TECHNICAL FIELD

The present invention relates to a kit for use in a regimen for treatment or prevention of osteoporosis. Specifically, the present invention relates to a kit for use in a regimen whereby a bone cell activating compound, a bone resorption inhibiting polyphosphonate, and a placebo or a nutrient supplement is administered sequentially to a subject afflicted with or at risk to osteoporosis.

Osteoporosis is the most common form of metabolic bone disease. Although it may occur secondary to a number of underlying diseases, 90% of all cases appear to be idiopathic.

Idiopathic osteoporosis is most commonly observed in postmenopausal women (postmenopausal osteoporosis) but it may also occur in elderly males and females (senile osteoporosis) or occasionally in younger individuals of both sexes. The disease which develops in postmenopausal women is characterized primarily by fractures of the wrist and spine, while femoral fractures seem to be the dominant feature of senile osteoporosis.

The fractures which occur in the various forms of osteoporosis are caused primarily by a gradual loss of bone which eventually reaches the point of mechanical failure. The physical nature of the bone which remains also seems to be compromised but the role which this plays in the loss of bone strength is unclear.

The mechanism by which bone is lost in osteoporotics is believed to involve the process by which the skeleton renews itself. This process has been termed bone remodeling. It occurs in a series of discrete pockets of activity. These pockets appear spontaneously within the bone matrix on a given bone surface as a site of bone resorption. There is apparently an activation of precursor cells within these pockets to form osteoclasts (bone dissolving or resorbing cells) which, in turn, resorb a portion of bone of generally constant dimensions. This process is followed by the appearance of osteoblasts (bone forming cells) which then refill the cavity left by the osteoclasts with new bone.

In a healthy adult subject, the rate at which osteoclasts and osteoblasts are formed is such that bone formation and bone resorption are in balance. However, in osteoporotics an imbalance in the bone remodeling process develops which allows bone to be lost at a rate faster than it is being made. Although this imbalance occurs to some extent in most individuals as they age, it is much more severe and occurs at a younger age in osteoporotics, particularly those who develop the postmenopausal form of the condition.

There have been many attempts to treat osteoporosis with a variety of pharmacologic agents with the goal being to either slow further bone loss or to produce a net gain in bone mass. It appears as though there are agents available which will slow further bone loss in osteoporotics but agents or methods of treatment which will result in the replacement of bone which has already been lost have been very elusive. The reason for this probably lies in the tight coupling characteristics of bone remodeling. Agents or methods of treatment which simulate or suppress one phase of the cycle (either resorption or formation) tend to have a similar effect on the opposing process. Therefore most attempts to treat osteoporosis have resulted in no more than a transient change and when the opposing process is stimulated or suppressed, the change is then negated.

Using a different approach, it has been attempted to induce bone activation by continuous administration of inorganic phosphate and to separately inhibit bone resorption by intermittent administration of calcitonin. This method has been shown to result in net bone formation in patients with post-menopausal osteoporosis. Furthermore, a theoretical model has been proposed which suggests that it may be possible to synchronize bone cell activity and metabolism by administering bone activating agents. Once synchronized, it should then be possible to limit the resorption by administering a bone resorption inhibiting agent during the natural life of the resorption phase of the bone remodeling units. The model does not address the problem of bone formation inhibition which is typically associated with the administration of a bone resorption inhibiting agent.

It is therefore an object of the present invention to provide a kit for treating osteoporosis which does not require a prolonged administration of pharmacologic agents, and which does not result in a significant inhibition of bone formation.

BACKGROUND OF THE INVENTION

U.S. Pat. No. 4,230,700, issued Oct. 28, 1980 to Francis, discloses the conjoint administration of certain polyphosphonate compounds, in particular diphosphonates, and vitamin D-like anti-rachitic compounds for inhibition of the anomalous mobilization of calcium phosphates in animal tissue. U.S. Pat. No. 4,330,537, issued May 18, 1982 to Francis, claims the compositions used in the methods of the U.S. Pat. No. 4,230,700. The patents specify that the administration of the phosphonate and the vitamin D-like compound be conjoint; moreover, the vitamin D-like compounds (unlike certain vitamin D metabolites) do not qualify as bone cell activating compounds.

Rasmussen et al., "Effect of Combined Therapy with Phosphate and Calcitonin on Bone Volume in Osteoporosis", *Metabolic Bone Disease and Related Research*, 2, 107 (1980), discloses a treatment regimen consisting of continuous administration of inorganic phosphate and intermittent administration of calcitonin. A net bone formation was observed.

Frost, "Treatment of Osteoporosis by Manipulation of Coherent Bone Cell Populations", *Clinical Orthopedics and Related Research*, 143, 227 (1979), discloses a theoretical model which suggests that it should be possible to synchronize the activity and metabolism of bone cells by administering bone cell activating agents. Once the cells have been synchronized, their resorption activity could be effectively inhibited by administration of a bone resorption inhibiting agent. The model requires that the bone resorption inhibiting agent be administered throughout the bone resorption phase of the bone remodeling unit. Furthermore, the model suggests that administration of a high dose of the bone resorption inhibiting agent is desirable because the bone resorption should be inhibited as much as possible. The model assumes that bone formation inhibition does not take place, because no bone resorption inhibiting agent is administered during the bone formation phase of the bone remodeling unit.

SUMMARY OF THE INVENTION

The present invention relates to a kit for use in a regimen for treatment or prevention of osteoporosis, said regimen comprising sequential administration of a bone cell activating compound, a bone resorption inhibiting polyphosphonate, and a placebo or a nutrient supplement, said kit containing the following components: (a) from 1 to about 5 daily doses of a bone cell activating amount each of a bone cell activating compound; (b) from about 10 to about 20 daily doses of from about $0.25 \times$ LED to about $3.3 \times$ LED each of a bone resorption inhibiting polyphosphonate; and (c) from about 30 to about 100 daily doses of a placebo or a nutrient supplement; and a means for having the components arranged in a way as to facilitate compliance with the regimen.

DETAILED DESCRIPTION OF THE INVENTION

The kit of the present invention is designed for use in a treatment regimen which consists of one or more cycles, whereby each cycle consists of a bone activating period, a bone resorption inhibition period and a rest period. During the bone activating period, bone cells are induced into a synchronized metabolism. During the bone resorption inhibition period, the bone resorption which naturally follows the activation is limited to a minimum by administration of a bone resorption inhibiting polyphosphonate. The rest period allows for natural bone formation to occur. It is desirable to administer food supplements, like calcium or vitamin D, during the rest period, so as to ensure optimum conditions for bone formation. If the administration of food supplements is deemed unnecessary, e.g., where the patient is on a fully controlled diet, the kit must contain daily doses of a placebo, to be taken during the rest period, so as to ensure a strict compliance with the regimen.

The preferred mode of administration is orally, but other modes of administration include, without limitation, intramuscular, intravenous, intraperitoneal, and subcutaneous administration, as well as topical application. All compounds described herein are administered orally, except where specified otherwise.

By "subject afflicted with or at risk to osteoporosis" as used herein is meant a subject diagnosed as suffering from one or more of the various forms of osteoporosis, or a subject belonging to a group known to have a significantly higher than average chance of developing osteoporosis, e.g., post-menopausal women, men over the age of 65, and persons being treated with drugs known to cause osteoporosis as a side effect (such as adrenocorticoid).

By "bone cell activating compound" as used herein is meant a compound which increases the rate of activation of new remodeling units on bone. The concept is described in more detail in Frost, *Clinical Orthopedics and Related Research,* 143, 227 (1979) and in Rasmussen et al., *Metabolic Bone Disease and Related Research,* 2, 107 (1980), the disclosures of which are incorporated herein by reference. In most cases this increased rate of activation is initially manifested by an increase in the number of bone resorbing cells and bone resorbing sites. Biochemical indicies of skeletal remodeling, such as urinary hydroxyproline levels, are expected to become elevated according to the magnitude of the response to the bone cell activating compound. Specific examples of such compounds are parathyroid hormone (PTH), inorganic phosphate, growth hormone, fluoride, thyroid hormone (e.g. thyroxine), certain vitamin D metabolites and prostaglandins. It may be possible to induce bone cell activation by non-chemical means, e.g. a strict, physical exercise regimen, or electrical currents.

By "bone cell activating amount" as used herein is meant an amount of the bone cell activating agent sufficient to effect a medically significant increase of the rate of activation of new remodeling units. If inorganic phosphate is used as the bone cell activating compound, the amount is in the range of from about 4 mg/kg/day to about 60 mg/kg/day (P.O.) of phosphorus, with amounts of from about 30 mg P/kg/day to about 50 mg P/kg/day preferred. Daily doses of inorganic phosphate should not exceed about 3.6 grams of phosphorus for any subject afflicted with or at risk to osteoporosis because severe diarrhea and gastrointestinal distress is likely to occur for dosages which exceed this amount.

Bone cell activating amounts of other bone cell activating compounds are as follows: 1,25-dihydroxy vitamin $D_3$ and other 1-hydroxy vitamin D metabolites: from about 0.001 microgram/kg/day to about 0.03 microgram/kg/day (P.O.); 25-hydroxy vitamin $D_3$ and other 25-hydroxy vitamin D metabolites (not including 1,25-dihydroxy vitamin D metabolites): from about 0.1 microgram/kg/day to about 3 microgram/kg/day (P.O.); inorganic fluoride (e.g. sodium fluoride): from about 0.1 mg/kg/day to about 1.0 mg/kg/day F per day (P.O.); thyroxine: from about 0.01 mg/kg/day to about 0.5 mg/kg/day (P.O.); triiodothyroxine: from about 0.1 microgram/kg/day to about 2.5 microgram/kg/day per day (P.O.); prostaglandin $PGE_2$: from about 0.1 to about 25 mg/kg/day (P.O.).

The ranges of daily doses of the above mentioned bone cell activating compounds for use in a kit of the present invention are therefore (assuming that the majority of subjects afflicted with or at risk to osteoporosis weigh between about 10 kg and about 100 kg): inorganic phosphate: from about 0.04 g P to about 3.6 g P (P.O.), from about 0.25 g P to about 3.6 g P (P.O.) preferred, with from about 2 g P to about 3 g P (P.O.) most preferred; 1,25-dihydroxy vitamin $D_3$ and other 1-hydroxy vitamin D metabolites: from about 0.01 micrograms to about 3 micrograms (P.O.), with from about 0.1 micrograms to about 2 micrograms (P.O.) preferred; 25-hydroxy vitamin $D_3$ and other 25-hydroxy vitamin D metabolites (not including 1,25-dihydroxy vitamin D metabolites): from about 1 microgram to about 300 micrograms (P.O.), with from about 10 micrograms to about 200 micrograms (P.O.) preferred; inorganic fluoride (e.g. sodium fluoride): from about 1 mg to about 100 mg (P.O.), with from about 10 mg to about 100 mg (P.O.) preferred; thyroxine: from about 0.1 mg to about 50 mg (P.O.), with from about 1 mg to about 25 mg (P.O.) preferred; triiodothyroxine: from about 1 microgram to about 250 micrograms (P.O.), with from about 10 micrograms to about 150 micrograms (P.O.) preferred; and prostaglandin $PGE_2$; from about 1 mg to about 2.5 g (P.O.), with from about 7.5 mg to about 2 g (P.O.) preferred.

By "bone resorption inhibiting polyphosphonate" as used herein is meant a polyphosphonate of the type disclosed in U.S. Pat. No. 3,683,080, granted Aug. 8, 1972, Francis, the disclosures of which are incorporated herein by reference. Preferred polyphosphonates are geminal diphosphonates (also referred to as bis-phosphonates). The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1-diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3-3-dimethyl-3-amino-1-hydroxy-1,1-diphosphonic acid, phenyl amino methane diphosphonic acid, N,N-dimethylamino methane diphosphonic acid, N(2-hydroxyethyl) amino methane diphosphonic acid, butane-4-amino-1-hydroxy-1,1-diphosphonic acid, pentane-5-amino-1-1hydroxy-1,1-diphosphonic acid, hexane-6-amino-1-hydroxy-1,1-diphosphonic acid and pharmaceutically acceptable esters and salts thereof.

The amount of the polyphosphonate to be used is determined entirely by its potency as a bone resorption inhibiting agent. This potency is determined by means of the thyroparathyroidectomized (TPTX) rat model described herein and expressed as the lowest effective dose (LED) of the compound which is defined as the lowest subcutaneously given dose of polyphosphonate, in mg P per kg body weight, which in the TPTX rat model results in an inhibition of the PTH-induced rise in serum calcium level. Since the amount of polyphosphonate to be administered is dependent on the bone resorption inhibition potency of the compound, the amount to be administered is conveniently expressed as multiples of LED. Extrapolation of the dosages for polyphosphonates from the TPTX rat model to humans is possible based on the observation that oral dosages in humans are porporationally related to the LEDs for polyphosphonates in the TPTX rat model. It is therefore observed that suitable amounts of polyphosphates for administration in subjects afflicted with or at risk to osteoporosis are from about 0.25×LED to about 3.3×LED, while amounts of from about 0.25×LED to about 2.5×LED are preferred, and amounts of from 0.50×LED to 2.0×LED are most preferred. The LEDs of a number of polyphosphonates are collected in Table I.

Ranges for the daily administration of some polyphosphonates for subjects afflicted with or at risk to osteoporosis are therefore: ethane-1-hydroxy-1,1-diphosphonic acid: from about 0.25 mg P/kg to about 3.3 mg P/kg, with from about 0.25 mg P/kg to about 2.5 mg P/kg preferred; dichloromethane diphosphonic acid: from about 0.12 mg P/kg to about 1.67 m P/kg, with from about 0.12 mg P/kg to about 1.25 mg P/kg preferred; propane-3-amino1-hydroxy-1,1-diphosphonic acid: from about 0.025 mg P/kg to about 0.33 mg P/kg, with from about 0.025 mg P/kg to about 0.25 mg P/kg preferred; butane-4-amino-1-hydroxy-1,1-diphosphonic acid: from about 0.0025 mg P/kg to about 0.033 mg P/kg, with from about 0.0025 mg P/kg to about 0.025 mg P/kg preferred; and hexane-6-amino-1-hydroxy-1,1-diphosphonic acid: from about 0.025 mg P/kg to about 0.33 mg P/kg, with from about 0.025 mg P/kg to about 0.25 P/kg preferred.

The ranges of daily doses of the above polyphosphonates for use in a kit of the present invention are therefore (assuming that the majority of subjects afflicted with or at risk to osteoporosis weigh between about 10 kg and about 100 kg): ethane-1-hydroxy-1,1-diphosphonic acid: from about 2.5 mg P to about 330 mg P, with from about 2.5 mg P to about 250 mg P preferred, from about 15 mg P to about 200 mg P more preferred, and from about 15 mg P to about 150 mg P most preferred; dichloromethane diphosphonic acid: from about 1.2 mg P to about 167 mg P, with from about 1.2 mg P to about 125 mg P preferred, from about 7 mg P to about 100 mg P more preferred, and from about 7 mg P to about 75 mg P most preferred; propane-3-amino-1-hydroxy-1,1-diphosphonic acid: from about 0.25 mg P to about 33 mg P, with from about 0.25 P to about 25 mg P preferred, from about 1.5 mg P to about 20 mg P more preferred, and from about 1.5 mg P to about 15 mg P most preferred; butane-4-amino-1-hydroxy-1,1-diphosphonic acid: from about 0.025 mg P to about 3.3 mg P, with from about 0.025 mg P to about 2.5 mg P preferred, from about 0.15 mg P to about 2.0 mg P more preferred, and from about 0.15 mg P to about 1.5 mg P most preferred; and hexane6-amino-1-hydroxy-1,1-diphosphonic acid: from about 0.25 mg P to about 33 mg P, with from about 0.25 mg P to about 25 mg P preferred, from about 1.5 mg P to about 20 mg P more preferred, and from about 1.5 mg P to about 15 mg P msot preferred.

By the term "nutrient supplement" as used herein is meant any compound which is generally considered to be a necessary component of a healthy diet and which, in the opinion of the attending physician, is not sufficiently or not consistently ingested by the subject as part of the meals. The term encompasses mixtures of such compounds. The reason why a nutrient supplement is administered to the subject is to make sure that the beneficial results of the regimen are not jeopardized by a poor diet. The most important compounds to be administered as nutrient supplements are therefore those involved in the formation of bone, e.g. vitamin D and calcium.

An important aspect of the present invention is the discovery that too high a dosage of polyphosphonate is detrimental to net bone formation. In fact, dosages which are routinely prescribed for the treatment of Pagets's disease appear on the high side for treatment in the present regimen. Generally, polyphosphonate dosage should not exceed about 3.3×LED/day, and are preferably below about 2.5×LED/day. Polyphosphonate dosages below 2.0×LED/day are most preferred.

Neither bone cell activating compounds nor bone resorption inhibiting polyphosphonate are administered during the rest period. This is not to say that no chemicals should be administered to the patient at all during this period. Food supplements like calcium and vitamin D (to be distinguished from bone cell activating metabolites of vitamin D) can beneficially be administered during this period.

Strict compliance with the above-described regimen is believed to be essential for its success. The kit of the present invention is designed to facilitate such strict compliance in that it contains a means for having the components arranged in a way as to facilitate compliance.

In one specific embodiment of the invention said means is a card having arranged thereupon the components of the treatment regimen in the order of their intended use. An example of such a card is a so-called blister pack. Blister packs are well known in the packaging industry, and are being widely used for the packaging of pharmaceutical unit dosage forms (tablets, capsules, and the like). Blister packs generally consist of a sheet of relatively stiff material, covered with a foil of a, preferably transparent, plastic material. During the packaging process, recesses are formed in the plastic foil. The recesses have the size and shape of the tablets or capsules to be packed. Next, the tablets or capsules are placed in the recesses, and the sheet of relatively stiff material is sealed against the plastic foil at the face of the foil which is opposite from the direction in which the recesses were formed. As a result, the tablets or capsules are sealed in the recesses, between the plastic foil and the sheet. Preferably, the strength of the sheet is such that the tablets or capsules can be removed from the blister pack by manually applying pressure on the recesses whereby an opening is formed in the sheet at the place of the recess. The tablet or capsule can then be removed via said opening.

It is desirable to provide a memory aid on the card, e.g. in the form of numbers next to the tablets or capsules, whereby the numbers correspond with the days of the regimen which the tablets or capsules so specified should be ingested. Another example of such a memory aid is a calendar printed on the card, e.g. as follows "First Week, Monday, Tuesday, . . . , etc. . . . Second Week, Monday, Tuesday, . . . ", etc. Other variations of memory aids will be readily apparent. A "daily dose" can be a single tablet or capsule or several pills or capules to be taken on a given day. Also, a daily dose of bone cell activating agent can consist of several tablets or capsules, while a daily dose of polyphosphonate is one tablet, or the other way around. The memory aid should reflect this.

The term "card", as used herein, is not limited to a flat, sheet-like structure. The term includes structures as described above which are folded so as to reduce their planar dimensions; the term further includes a plurality of cards which, combined, contain the components for the treatment regimen. An example of the latter would be a stack of cards, marked "Week 1", "Week 2", etc., each containing the components of the regimen for one week of treatment. The tablets or capsules may also be arranged on a narrow strip, one after the other; the material of the strip is preferably flexible, so that it can be wound on a reel. The strip may be perforated so that daily doses can be torn off.

In another specific embodiment of the invention said means is a dispenser designed to dispense said daily doses, one at a time, in the order of their intended use. Preferably, the dispenser is equipped with a memory-aid, so as to further facilitate compliance with the regimen. An example of such a memory-aid is a mechanical counter which indicates the number of daily doses that has been disposed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Single-unit dispensers are well known and are being widely used in, e.g., vending machines. The concepts of such machines are directly suitable for, or easily adaptable to, use in the dispensers of this embodiment of the present invention.

THYROPARATHYROIDECTOMIZED (TPTX) RAT MODEL

To determine the bone resorption inhibition potency of several polyphosphonates, the following animal model was used.

In this study 50 male Wistar rats weighing approximately 150–160 grams were thyroparathyroidectomized surgically by the breeder (Charles River Breeding Laboratories). All rats were double housed on arrival in suspended cages with Purina Laboratory Rodent Chow $^R$ and tap water ad libitum. After acclimation to the laboratory environment for 3–5 days, the rats were placed on a low calcium, low phosphorous (0.18%/0.22%) diet (Teklad $^R$) and given 2% (W/V) calcium gluconate supplemented deionized water via water bottles.

On day four of low-calcium diet all rats were anesthetized with Ketaset $^R$ (Ketamine Hydrochloride, 100 mg/ml, Bristol Myers), 0.10 ml/100 grams of body weight, weighed and then bled orbitally for serum total calcium analysis using Flame Atomic Absorption (FAA). All rats weighing less than 180 grams were eliminated from study. Animals were then randomized statistically such that the means total calcium for each group was the same. Only rats deemed hypocalcemic (total calcium $\leq 8.0$ mg/dl) were placed in study groups (6 animals in each group).

Treatments with various experimental compounds comenced on day 6 and lasted through day 9 of the study (at 1:00 P.M. each day). Dose solutions were prepared to be given at a constant rate of 0.2 ml/100 grams of body weight subcutaneously in the skin flap where the hind leg meets the torso. All rats were weighed and dosed daily. A 25 gauge ⅝" needle was used to administer drug, alternating dose sites daily. On day 9 all rats were fasted in the afternoon at approximately 4:00 P.M. On day 10 of study no treatment was given. In the morning a 600 $\mu$l sample of whole blood was collected from each rat in Microtainer (B-D#5060) serum separater tubes for serum total calcium (FAA). Two 125 $\mu$l samples of heparinized whole blood were also collected to be used for ionized calcium analysis (radiometer ICA1). Immediately following blood collection all rats were weighed and injected and bovine parathyroid hormone subcutaneously at a rate of 75 USP (filtered) per 100 grams of body weight. Blood sampling for total and ionized calcium was repeated three hours post-PTH injection.

STATISTICS

All pre- and post-PTH total and ionized calciums were statistically analyzed for significance compared to PTH alone (control) using Student's t-test, analysis of variance, and their non-parametric equivalents. The post minus pre-change and % change were also determined on calcium levels and pre-drug vs post-drug body weights.

MATERIALS

Low calcium and phosphorous diets used were prepared by Teklad $^R$ Test Diets (Harlan Industries, Madison, Wis. 53711; Order #TD82195) in a pellet form of approximately 0.18% calcium and 0.22% phosphorous. The diets contained all the essential vitamins and minerals required for the rat, with the exception of calcium and phosphorus. The calcium and phosphorous levels of the pellets were verified analytically.

All dosing solutions of compounds to be tested for bone resorption inhibition potency were adjusted to pH 7.4 with sodium hydroxide and prepared in 0.9% saline (Abbott NDC 0074-1583-03), Abbott Labs, North Chicago, Ill. 60064, U.S.A). Dosing solution concentrations were adjusted to a dosing rate of 0.20 ml/100 grams of body weight.

PTH was acquired as a powdered bovine extract (Sigma Chemical Co., P.O. Box 14508, St. Louis, Mo., order #P-0892, Lot #72F-9650) at an activity of 138 USP units per mg. PTH was prepared in 0.9% saline such that the final concentration was 100 U.S.P./ml. All solutions were filtered through a #40 Whatman Filter Paper then 0.45 μm Metricel $^R$ filter.

The physiological effect of the PTH challenge is a rise in serum calcium level. Since the animals were on a low calcium diet, an observed increase in serum calcium level is the result of a resorption of bone material. Since polyphosphonates tend to inhibit resorption of bone material, the animals pretreated with polyphosphonate showed a rise in serum calcium level upon PTH challenge which was less than that found in control animals which had been treated with saline vehicle instead. The lowest dose at which the polyphosphonate is capable of inhibiting bone resorption, as evidenced by a decreased rise in serum calcium upon PTH challenge, is a measure of the bone resorption inhibition potency of the polyphosphonate. Where necessary the test was repeated, whereby the animals were administered with 0.5 and 0.2×LED, in order to refine the determination of LED. The LED values of some representative diphosphonates are presented in Table I.

TABLE 1

| Lowest Effective (antiresorptive) Dose (LED) Values | |
|---|---|
| Compound* | LED (mg P/kg) |
| ethane-1-hydroxy 1,1-diphosphonic acid (EHDP) | 1.0 |
| dichloromethane diphosphonic acid (Cl$_2$MDP) | 0.5 |
| propane-3-amino-1-hydroxy-1,1-diphosphonic acid (APD) | 0.10 |
| butane-4-amino-1-hydroxy-1,1-diphosphonic acid (ABDP) | 0.01 |
| hexane-6-amino-1-hydroxy-1,1-diphosphonic acid (AHDP) | 0.10 |

*All compounds were in aqueous solution, the pH of which had been adjusted to 7.4 with NaOH. At this pH the diphosphonic acids are present as their disodium salts.

CLINICAL TEST

Five patients clinically diagnosed as suffering from osteoporosis were subjected to a treatment regimen according to the present invention as follows. Each patient was subjected to from 3 to 8 cycles, each cycle consisting of (a) a bone activating period of 3 days during which 2 tablets of Phosphate Sandoz TM were administered 3 times daily (each tablet contains 500 mg of elemental phosphorus); (b) a bone resorption inhibition period of 14 days during which the patients received 5 mg/kg/day (corresponding to 1.24 mg P/kg/day, or 1.24×LED) of DIDRONEL (Norwich Eaton Pharmaceuticals, Norwich, N.Y.) divided into 3 doses (each DIDRONEL tablet contains 200 mg of disodium EHDP); (c) a rest period of 73 days during which the patients received a diet which was verified by dieticians to contain a minimum of 1 g/day of calcium. Each patient was examined clinically before the following cycle was instituted. All patients were subjected to a standardized double tetracycline labeled transiliac crest bone biopsy before starting the treatment and after 3, 6 or 8 cycles were completed. The bone biopsy is described in detail by Melsen et al., "The Role of Bone Biopsy in the Diagnosis of Metabolic Bone Disease," Orthop. Clin. of NA, 12, 571-602 (1981), the disclosures of which are incorporated herein by reference. All bone biopsies were prestained with osteochrome stain as described by Villanueva in "Theory and Practice of Histotechnology," 2nd Ed., C.V. Mosley Co., London, 1980, pp. 100-101, the disclosures of which are incorporated herein by reference. The biopsies were then embedded in methacrylate as described by Anderson in "Manual for the Examination of Bone," CRC Press, 1982, pp. 27-29, the disclosures of which are incorporated herein by reference. Twenty sections were cut on a Jung K heavy duty Microtome, ten sections of each biopsy were stained with toluidine blue and ten sections remained unstained for viewing with ultraviolet light. Histomorphometric analyses of static and dynamic parameters of trabecular bone were carried out twice by two individuals on each biopsy using a Zeiss Photomicroscope III with the necessary attachment to use the osteoplan semi-automatic method as described by Malluche et al., Calcif. Tissues, Int., 1982, 34, 439-448, the disclosures of which are incorporated herein by reference.

All patients reported subjective improvement in their symptomatology and a marked increase in their daily physical activity with less periods spent at forced rest because of pain. The patient who had been subjected to 3 cycles of therapy showed a directional improvement in trabecular bone mass. The three patients who had been subjected to 6 cycles and the one patient who had been subjected to 8 cycles showed a dramatic improvement in their trabecular bone mass, their trabecular diameter, as well as a dramatic improvement in the dynamic assessment of their trabecular bone remodeling activity as measured by histomorphometric analyses of transiliac crest biopsies. These results indicate that there was a significant improvement in the osteoporotic condition of these patients.

Other osteoporotic patients were subjected to a similar regimen, except that the daily dosage of disodium EHDP during the bone resorption inhibition period was 15 mg/kg/day (3.72×LED). No significant increase of bone mass was observed. These results indicate that the treatment regimen of the present invention results in a dramatic increase of trabecular bone mass, but that a daily dosing of polyphosphonic acid in excess of 3.3×LED is counterproductive.

The treatment regimen is varied as indicated in Table II.

TABLE II

| Bone Activating Period | | | Bone Resorption Inhibition Period | | | Rest Period Days | Total Cycle Days |
|---|---|---|---|---|---|---|---|
| Days | Compound | Dose/day | Days | Compound | Dose/day (mg P/kg) | | |
| 1 | 1,25-Vit. D[a] | 1 ug | 10 | Cl$_2$MDP | 2.5 | 30 | 41 |
| 3 | NaF | 20 mg | 12 | APD | 0.5 | 40 | 55 |
| 5 | PTH 1-34[b] | 100 ug | 17 | AHDP | 0.03 | 50 | 72 |

TABLE II-continued

| Bone Activating Period | | | Bone Resorption Inhibition Period | | | Rest Period Days | Total Cycle Days |
|---|---|---|---|---|---|---|---|
| Days | Compound | Dose/day | Days | Compound | Dose/day (mg P/kg) | | |
| 4 | PGE$_2$(c) | 10 mg/kg | 20 | ABDP | 0.005 | 80 | 104 |

(a)1,25 dihydroxy vitamin D$_3$
(b)parathyroid hormone 1-34
(c)prostaglandin E$_2$ A treatment regimen consisting of one or more of the above cycles results in an appreciable alleviation of osteoporotic conditions.

EXAMPLE I

A kit for use in a regimen for treatment or prevention of osteoporosis is made up as follows:

A slip case 4¾" wide × 8½" high × 5½" deep (about 12 cm × 21½ cm × 14 cm) contains 10 cards (blister packs) of 4¾" × 8½" (about 12 cm × 2½ cm). The first card has arranged thereupon 3 rows of 6 tablets each. Each tablet contains inorganic phosphate, 500 mg phosphorus per tablet. The rows are marked (from left to right) "Day 1", Day 2", and "Day 3" and the patient is instructed to take two tablets three times per day (i.e., the total daily dose consists of 6 tablets of 500 mg P each).

The second card contains 14 tablets, each tablet containing 400 mg EHDP (DIDRONEL), Norwich Eaton Pharmaceuticals, Norwich, N.Y.). The tablets are arranged in 4 rows of 3 tablets each and a 5th row of 2 tablets. Printed on the card, next to each tablet, are the words "Day 4", "Day 5", . . . etc. through "Day 17".

The remaining 8 cards each contain 20 capsules, each capsule containing 300 mg of calcium and 200 units of vitamin D. Printed on each card are rectangular boxes, such that each box contains two capsules (i.e., 10 boxes per card; one daily dose is two capsules, each of which contains 300 mg of calcium and 200 units of vitamin D). The boxes are marked "Day 18", "Day 19", etc., through "Day 97"on the last card.

The last card further contains a printed reminder that a renewal prescription should be obtained.

Similar kits are put together wherein the 3 daily doses of inorganic phosphate are replaced with daily doses of other bone cell activating compounds. For example: 5 daily doses of 0.5 microgram each of 1,25-dihydroxy vitamin D$_3$; 2 daily doses of 100 micrograms each of 25-hydroxy vitamin D$_3$; 4 daily doses of 80 mg F each of inorganic fluoride; 1 daily dose of 20 mg thyroxine; 3 daily doses 70 micrograms each of triiodothyroxine; or 4 daily doses of 50 mg each of prostaglandin PGE$_2$.

Similar kits are further made by replacing the 14 daily doses of sodium ethane-1-hydroxy-1,1-diphosphonate ("EHDP") with daily doses of other bone resorption inhibiting polyphosphonates. For example: 10 daily doses of 20 mg P each of dichloromethane diphosphonic acid; 18 daily doses of 8 mg P each of propane-3-amino-1-hydroxy-1,1-diphosphonic acid; 20 daily doses of 0.7 mg P each of butane-4-amino-1-hydroxy-1,1-diphosphonic acid; or 15 daily doses of 10 mg P each of hexane-6-amino-1-hydroxy-1,1-diphosphonic acid.

Similar kits are further made by replacing the 80 daily doses of calcium and vitamin D with, e.g., 60 daily doses of 500 mg each of calcium; 40 daily doses of 400 units each of vitamin D; or 30 daily doses of one placebo tablet each.

What is claimed is:

1. A kit for use in a regimen for treatment or prevention of osteoporosis, said regimen comprising sequential administration of a bone cell activating compound, a bone resorption inhibition polyphosphate, and a placebo, or a nutrient supplement, said kit containing the following components:
   (a) from 1 to about 5 daily doses of a bone cell activating amount each of a bone cell activating compound;
   (b) from about 10 to about 20 daily doses of from about 0.25 mgP/kg/day to about 3.3 mgP/kg/day of ethane-1-hydroxy-1,1-diphosphonic acid, or a pharmaceutically-acceptable salt or ester thereof;
   (c) from about 30 to about 100 daily doses of a placebo or a nutrient supplement;
and a means for having the components arranged in a way as to facilitate compliance with the regimen.

2. The kit of claim 1 wherein the daily doses of the ethane-1-hydroxy-1,1-diphosphonic acid, or a pharmaceutically-acceptable salt or ester thereof, are from about 0.25 mgP/kg/day to about 2.5 mgP/kg/day.

3. The kit of claim 1 wherein said means is a card having arranged thereupon said components in the order of their intended use.

4. The kit of claim 2 wherein said means is a card having arranged thereupon said components in the order of their intended use.

5. The kit of claim 1 wherein said means is a dispenser designed to dispense said daily doses, one at a time, in the order of their intended use.

6. The kit of claim 2 wherein said means is a dispenser designed to dispense said daily doses, one at a time, in the order of their intended use.

7. The kit of claim 2 wherein the bone cell activating compound is an inorganic phosphate and each daily dose is from about 250 mg P to about 3.6 g P.

8. The kit of claim 7 wherein the bone cell activating compound is an inorganic phosphate and each daily dose is from about 2 g P to about 3 g P.

9. The kit of claim 2 wherein the bone cell activating compound is 1,25-dihydroxy vitamin D$_3$ and each daily dose is from about 0.1 microgram to about 2 micrograms.

10. The kit of claim 2 wherein the bone cell activating compound is 25-hydroxy vitamin D$_3$ and each daily dose is from about 10 micrograms to about 200 micrograms.

11. The kit of claim 2 wherein the bone cell activating compound is an inorganic fluoride and each daily dose is from about 10 mg F to about 100 mg F.

12. The kit of claim 2 wherein the bone cell activating compound is thyroxine and each daily dose is from about 1 mg to about 25 mg.

13. The kit of claim 2 wherein the bone cell activating compound is triiodothyroxine and each daily dose is from about 10 micrograms to about 150 micrograms.

14. The kit of claim 2 wherein the bone cell activating compound is prostaglandin PGE$_2$ and each daily dose is from about 7.5 mg to about 2 g.

15. The kit of claim 1 wherein the daily dose of ethane-1-hydroxy-1,1-diphosphonic acid, or a pharmaceutically-acceptable salt or ester thereof, is from about 15 mg P to about 200 mg P.

16. The kit of claim 15 wherein the daily dose of ethane-1-hydroxy-1,1-diphosphonic acid, or a pharmaceutically-acceptable salt or ester thereof, is from about 15 mg P to about 150 mg P.

17. A kit for use in a regimen for treatment or prevention of osteoporosis, said regimen comprising, sequential administration of inorganic phosphate, ethane-1-hydroxy-1,1-diphosphonic acid or a pharmaceutically acceptable salt thereof, and a mixture of vitamin D and calcium, said kit containing the following components:
- (a) a card having arranged thereupon 3 daily doses of inorganic phosphate, each daily dose containing about 2000 mg P;
- (b) a card having arranged thereupon 14 daily doses of about 100 mg P each of ethane-1-hydroxy-1,1-diphosphonic acid, or a pharmaceutically acceptable salt or ester thereof;
- (c) a plurality of cards containing about 73 daily doses, each dose containing about 500 mg calcium.

* * * * *

UNITED STATES PATENT AND TRADEMARK OFFICE
CERTIFICATE OF CORRECTION

PATENT NO. : 4,812,311
DATED : March 14, 1989
INVENTOR(S) : Vernon A. Uchtman

It is certified that error appears in the above-identified patent and that said Letters Patent is hereby corrected as shown below:

Column 6, line 27, "msot" should be --most--.
Column 12, line 13, "inhibition polyphosphate" should be --inhibiting polyphosphonate--.

Signed and Sealed this

Thirty-first Day of October, 1989

Attest:

DONALD J. QUIGG

*Attesting Officer*   *Commissioner of Patents and Trademarks*